United States Patent
Ebert et al.

(10) Patent No.: US 8,332,018 B2
(45) Date of Patent: Dec. 11, 2012

(54) METHOD AND ARRANGEMENT TO PREDICT AT LEAST ONE SYSTEM EVENT AND A CORRESPONDING COMPUTER PROGRAM AND A CORRESPONDING MACHINE-READABLE STORAGE MEDIUM

(75) Inventors: Manuel Ebert, Baiersdorf (DE); Daniel Bast, Obernburg (DE); Thomas Kraemer, Nuremberg (DE); Sergey Berdyshev, Baiersdorf (DE); Wolfgang Meyer, Erlangen (DE)

(73) Assignee: BIOTRONIK CRM Patent AG, Baar (CH)

( * ) Notice: Subject to any disclaimer, the term of this patent is extended or adjusted under 35 U.S.C. 154(b) by 165 days.

(21) Appl. No.: 12/757,350

(22) Filed: Apr. 9, 2010

(65) Prior Publication Data
US 2010/0262027 A1    Oct. 14, 2010

Related U.S. Application Data

(60) Provisional application No. 61/232,012, filed on Aug. 7, 2009.

(30) Foreign Application Priority Data

Apr. 9, 2009    (DE) .................. 10 2009 002 307
Jan. 18, 2010    (DE) .................. 10 2010 000 103

(51) Int. Cl.
*A61B 5/04*    (2006.01)
*A61B 5/00*    (2006.01)
*A61B 5/02*    (2006.01)

(52) U.S. Cl. ........ 600/509; 600/300; 600/508; 600/515; 600/516; 600/517; 600/518

(58) Field of Classification Search .................. 600/300, 600/508, 509, 515–518
See application file for complete search history.

(56) References Cited

U.S. PATENT DOCUMENTS
2008/0188763 A1*    8/2008    John et al. .................. 600/516

* cited by examiner

*Primary Examiner* — Niketa Patel
*Assistant Examiner* — William Levicky
(74) *Attorney, Agent, or Firm* — Buchanan Ingersoll & Rooney PC

(57) ABSTRACT

A method, a system and an arrangement to predict at least one system event and a corresponding computer program and a corresponding machine-readable storage medium are configured so that the event is predictable because of trends in observables over a certain period before the occurrence of the events. The method, system and arrangement can be used in particular for patient-specific monitoring of patho-physiological changes but also in geophysical or abstract units such as population or economic systems in which the deviation from a defined normal condition is predicted.

17 Claims, 6 Drawing Sheets

METHOD AND ARRANGEMENT TO PREDICT AT LEAST ONE SYSTEM EVENT AND A CORRESPONDING COMPUTER PROGRAM AND A CORRESPONDING MACHINE-READABLE STORAGE MEDIUM

CROSS-REFERENCE TO RELATED APPLICATIONS

This application claims the priority of German Patent Application No. DE 10 2009 002 307.0, filed on Apr. 9, 2009 in the German Patent Office, U.S. Provisional Patent Application No. 61/232,012, filed on Aug. 7, 2009 in the U.S. Patent Office, and German Patent Application No. DE 10 2010 000 103.1, filed on Jan. 18, 2010 in the German Patent Office, the disclosures of which are incorporated herein in their entirety by reference.

FIELD OF THE INVENTION

The present invention is directed towards predicting system events in complex systems.

BACKGROUND OF THE INVENTION

The object of the invention is a method and arrangement to predict at least one system event and a corresponding computer program and a corresponding machine-readable storage medium, where the event is predictable because of trends in observables over a certain period of time before the occurrence of the events. The invention can be used in particular for patient-specific monitoring of patho-physiological changes. The method can be used both in linear and non-linear sequences as well as disjunctions in the observables. An event may be, for example, the failure of a system, because the abnormal behavior of a certain component is expressed in the irregularities of one or more observables or the early recognition or pre-acute prediction of a particular critical condition of a patient, for example. The systems themselves may also represent geophysical or abstract units such as population or economic systems in which the deviation from a defined normal condition is predicted.

In the case of complex processes, or systems, events are triggered by numerous factors. Such factors may appear in various manners so that different kinds of behavior of factors can lead to the same event. Prediction of events, such as a so-called decompensation among cardiac patients, has therefore been possible only with a high degree of imprecision up to now.

It is therefore the purpose of the present invention to provide a method and arrangement to predict at least one system event and a corresponding computer program and a corresponding machine-readable storage medium for the prediction of an event that avoid the above-mentioned disadvantages and are, in particular, robust in coping with heterogeneous signal progressions before certain events.

SUMMARY OF THE INVENTION

According to the invention, a method and system is provided for the prediction of system events that captures measured values $s_j$ of at least one primary parameter $S_j$ within at least one time window. The length of the time windows can be preset $L \in N$ within a range of a minimum length $L_{min} \in N$ to a maximum length $L_{max} \in N$, and begin at presettable times $H \in N$. The variable H describes the delay time between the time of the prediction and the occurrence of the predicted event, e.g., the time until the actual or expected occurrence of the upcoming system event, and runs from $H_{min} \in N$ to $H_{max} \in N$. For at least one part of such time windows and for at least one part of the primary parameters $S_j$, the probability of the existence of a trend is determined. Moreover, for at least one part of the time windows and for at least one part of the primary parameters $S_j$, a value is determined for the relevance (relevance value) of that window for prediction. Preferably, at least the discriminatory power of the time window for the primary parameters $S_j$ will be determined. For at least one part of captured primary parameters $S_j$ and for at least one part of the time windows, at least one feature will then be constructed, where the construction of at least one such feature will at least take into account part of the probabilities of a trend $p_j$ and the relevance values. Such probabilities may be taken into account in such a way that the probabilities of a trend $p_j$ are correlated with the relevance values through appropriate arithmetic operations. For example, a weighting of the probabilities of a trend $p_j$ as a function of the relevance values and/or a summation of the (weighted) probabilities of a trend $p_j$ may be provided. In one advantageous embodiment, the relevance value takes into account the discriminatory power of the time window for the primary parameter $S_j$. The feature undergoes a classification method that yields an indicator for the occurrence or non-occurrence of a system event. As a function of that indicator, the system event is signaled and/or system-event-related measures are initiated.

Embodiments of the invention use a multiple parameter set for which trend analysis is used to determine features for individual primary parameters $S_j$, which then undergo a classification method. Each feature is based on at least one primary parameter $S_j$. In one advantageous embodiment, all probabilities of a trend $p_j$ are used for identification of areas with maximal discriminatory power. That is then used to derive all the relevant window lengths and positions. In such windows, it is preferable that all probabilities be combined (rather than only the probabilities above a certain threshold value). That combination then represents a feature for a classification method from which each primary parameter $S_j$ can then be formed in turn.

Thus, when the invention is used, a system's signal progression is checked for a certain form of variability within a limited period of time before an event that is to be detected, while the probability of existence of trends is calculated from time windows that begin a certain time before the time of prediction and have a given length. Those probabilities of selected time windows are combined. Such a combination should preferably be calculated for all measurands. A suitable synthesis of the combinations can then be made, if need be, and features can be constructed. The classification method used in that case will either be optimized with the help of data with known properties or else used on unfamiliar data and the result of the process will be analyzed with the aid of an automatically or manually determined decision boundary.

With the aid of such an appropriate classification method, an indicator is supplied by means of which it can be concluded that an event will (or will not) occur. Such an indicator signals an upcoming event. Such events may be a critical system event, for example. Such critical system events may be, but are not limited to, for example, arrhythmias, pulmonary embolisms, cerebro-vascular accident, myocardial infarction, angina pectoris, syncope, transient ischemic attack and/or acute peripheral arteriosclerotic disorders.

Various courses of action may be deduced from the result, such as triggering an alarm that indicates the malfunctioning of a system or deviations from normal behavior, sets automated maintenance or substitution processes in motion, reports deterioration of an illness to the doctor or patient, initiates a supporting therapy, e.g., a shock or change of the pacing scheme (stimulation scheme) or permits the initiation of similar urgent measures, in order to avoid damage to the system, failure of the system or the death of the patient.

The invention provides a method and system for the prediction of future system events. The predictions are then made on the basis of primary parameters that were captured within a limited time period before the time of prediction, while the primary parameters that characterize the system in a certain time period are used to form features that reflect the change of the system. The prediction time period may be limited before and after and does not necessarily have to begin at the time of prediction.

To that purpose, at least one time window of length L is observed within the observation period. Within the time window, measured values $s_j$ of at least one primary parameters $S_j$ are captured. The measured values at the points of measurement of the primary parameters before the time of prediction are applied in chronological order.

For at least one part of the time windows, a combination of the probabilities of a trend is determined for at least one part of at least one primary parameter $S_j$. Upward or downward trends may be considered together or separately.

Embodiments of the invention therefore provide for signaling a system event and/or initiating one or more system-event-related measures based on the probabilities of a trend of time windows. That may be achieved, for example, by analyzing the combination of probabilities of a trend of time windows in a classification method and predicting at least one system event based on the classification. Such measures may involve system-stabilizing measures, for example, such as a change of medicines and/or other therapeutic support measures, automated maintenance and/or substitution processes.

One advantageous embodiment provides for optimizing the classification method by using classified event data and/or control data.

According to another advantageous embodiment, determination of a trend includes testing a hypothesis for the existence of a trend. It is preferable to perform the Mann trend test in that respect. Other trend test methods may be used, but the Mann test is more robust in coping with outliers than many other methods.

According to yet another advantageous embodiment, in order to determine the trend, different trend test methods are used for different primary parameters, depending on the features of the primary parameters.

According to another advantageous embodiment, not only the determination of the trend but also the related trend strength is considered.

Preferably, the measured values (=test signals) $s_j$ of at least one primary parameter $S_j$ are captured at certain time intervals. The units of the time intervals may be seconds, minutes, hours, days, weeks, months or years, with the possibility of using various time intervals for the various primary parameters.

The invention can be used, for example, to analyze heterogeneous signal progressions. The signal progressions may be linear or non-linear or contain disjunctions.

A further advantage of the invention is that the method is robust in coping with data gaps.

Examples of possible primary parameters include, but are not limited to:

all primary parameters that include the patient's heart rate, such as the heart rate over a predetermined time period, the heart rate during a specified phase of rest, the variability of the heart rate, and so on;

all primary parameters that determine impedances in the patient, whether through intracranial (bipolar and multipolar) or intrathoracic measurements or by determination using external sensors;

all primary parameters that determine the patient's activity in any way;

all primary parameters that receive as input the percentage of left- or right-ventricular events, whether stimulated, perceived or otherwise;

all primary parameters that record implant-dependent signals;

all primary parameters that determine extrasystoles, irrespective of place of origin thereof;

all primary parameters that register a patient's hemodynamics or other elasticities, pressures, volumes or intervals;

all primary parameters that are determined outside an implant, such as measured quantities that are acquired from radio-linked sensors, or measured quantities from devices that record data external to the body and communicate such data telemetrically to the evaluation unit;

all biomedical primary parameters, such as stimulation thresholds, electrode configurations, sensor amplifications or offset values;

all primary parameters such as blood sugar levels, other biomarkers or similar quantities;

all primary parameters that determine biometric information about the patient;

all primary parameters that record additional information about medication;

all primary parameters that are determined by electrophysiological or biochemical processes;

all primary parameters that record signals from imaging, acoustic or mechanical processes;

all of the aforementioned primary parameters that are normalized and/or scaled in advance; and all possible combinations of several of the aforementioned primary parameters.

One arrangement according to the invention has at least one chip and/or processor and is configured in such a way that a method for the prediction of at least one system event is feasible, where the method includes at the least the following steps:

Capture of measured values $s_j$ of at least one primary parameter $S_j$ within at least one time window of a length that can be set in advance, for at least one part of the captured primary parameters $S_j$, determining the probability of a trend $p_j$ for a number of time windows that can be set in advance, for at least one part of the captured primary parameters $S_j$, determining a value for the relevance of the time window for the prediction of at least one system event, for at least one part of the captured primary parameters $S_j$ and for at least one part of the time windows, constructing at least one feature M to describe the system through analysis of the probability of a trend $p_j$ and of the value for the relevance of the time window, classification of at least one feature M, and signaling of a system event and/or initiation of system-event-related measures according to the results of the classification.

It should be understood that the chip and/or processor may include memory coupled to the chip and/or processor that has coding or software stored thereon for executing the method.

A computer program for prediction of system events enables a data processing installation, after said program has been loaded into the memory of the data processing installation, to carry out a method for predicting at least one system event, where the method includes at least the following steps:

Capture of measured values $s_j$ of at least one primary parameter $S_j$ within at least one time window of a length that can be set in advance, for at least one part of the captured primary parameters $S_j$, determining the probability of a trend $p_j$ for a number of time windows that can be set in advance, for at least one part of the captured primary parameters $S_j$, determining a value for the relevance of the time window for the prediction of at least one system event, for at least one part of the captured primary parameters $S_j$ and for at least one part of the time windows, constructing at least one feature M to describe the system through analysis of the probability of a trend $p_j$ and of the value for the relevance of the time windows, Classification of at least one feature M and Signaling of a system event and/or initiation of system-event-related measures according to the results of the classification.

According to another advantageous embodiment of the invention, the computer program according to the invention has a modular design, with individual modules installed on different data processing installations.

Advantageous embodiments provide for additional computer programs through which additional process steps or process sequences stated in this description can be carried out.

Such computer programs might be downloadable, for example (for a fee or free of charge, freely accessible or password-protected), from a data or communication network. The computer programs made available in that manner can be made useable through a method in which a computer program is downloaded from an electronic data network, such as the Internet, to a data processing installation connected to a network.

In order to carry out the method according to the invention for prediction of system events, use of a machine-readable storage medium is contemplated on which a program is stored that enables a data processing installation, after said program has been loaded into the memory of the data processing installation, to carry out a method for predicting at least one system event, where the method includes at least the following steps:

Capture of measured values $s_j$ of at least one primary parameter $S_j$ within at least one time window of a length that can be set in advance, for at least one part of the captured primary parameter $S_j$, determining the probability of a trend $p_j$ for a number of time windows that can be set in advance, for at least one part of the captured primary parameters $S_j$, determining a value for the relevance of the time window for the prediction of at least one system event, for at least one part of the captured primary parameters $S_j$ and for at least one part of the time windows, constructing at least one feature M to describe the system through analysis of the probability of a trend $p_j$ and of the value for the relevance of the time windows, classification of at least one feature M, and signaling of a system event and/or initiation of system-event-related measures according to the results of the classification.

It should be appreciated that one example of a data processing installation is a computer device for running a computer program.

BRIEF DESCRIPTION OF THE DRAWINGS

We shall now proceed to explain in greater details some advantageous embodiments of the invention with respect to the drawings.

METHODS

Fundamental Calculation (Feature Construction):

In the first step, the incoming test signals $s_j$ of the measurand $S_j$ are filtered. The measurand $S_j$ where $j=1, \ldots, N^S$ is then used as a so-called primary parameter for the construction of the feature. The number of primary parameters is designated as $N^S$ (superscripted signs and numerals are indices, unless noted otherwise). In the first step, a check is performed to determine, among other things, whether the values of the measurands lie within a valid range of values.

Figure 1:
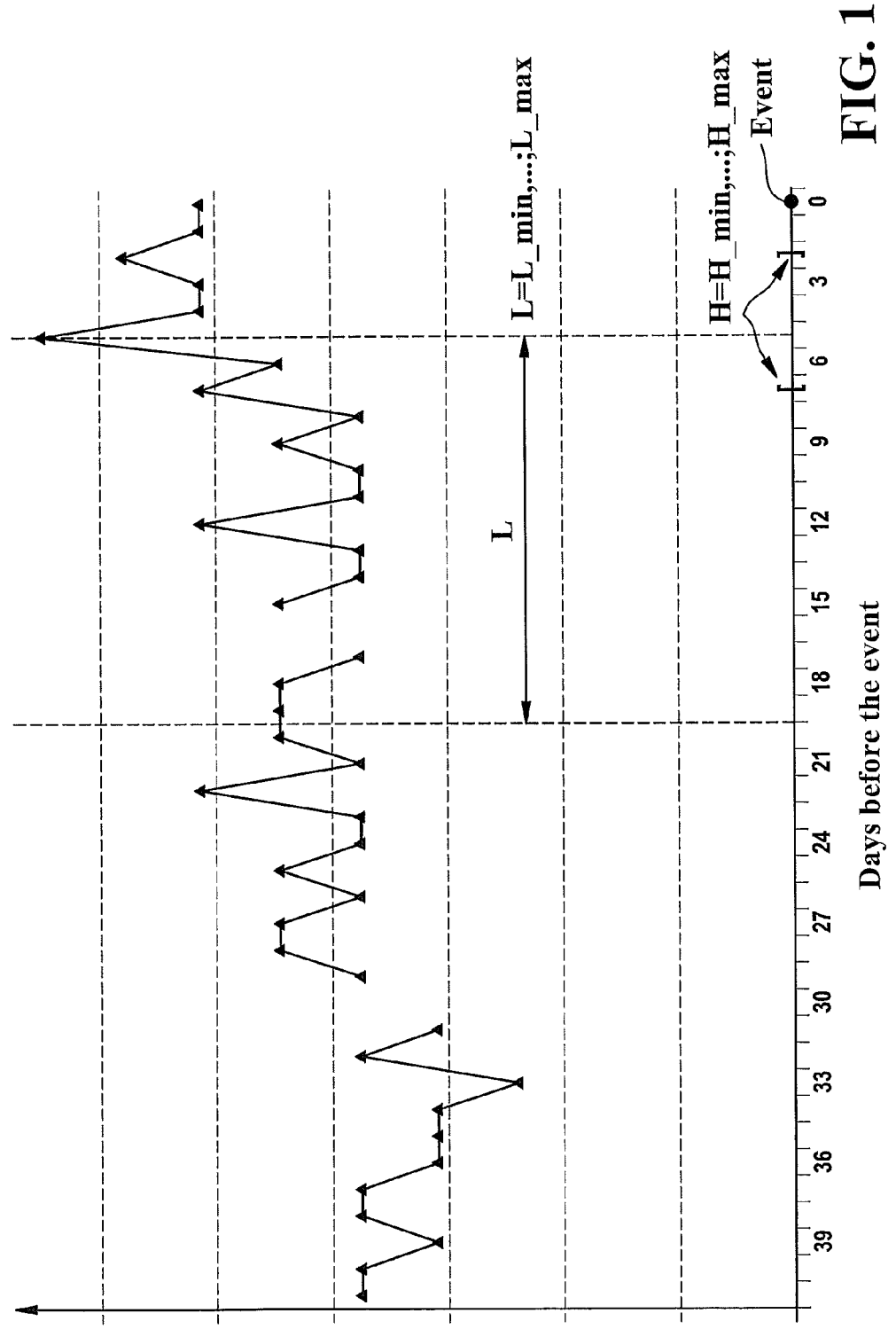
FIG. 1 is a description of the parameters $L_{min}$, $L_{max}$, $H_{min}$ and $H_{max}$.

In principal, the time sequence of the test signals generally depends on two parameters whose meaning is illustrated in FIG. 1. The variable $L \in N$ represents an observation window between the lengths $L_{min} \in N$ and $L_{max} \in N$, in the course of which the variability of a test signal is checked. The variable $H \in N$ describes the delay time between the time of the prediction and the occurrence of the predicted event, e.g., the time until the actual expected occurrence of the upcoming decompensation process and runs from $H_{min} \in N$ to $H_{max} \in N$. A suitable criterion should then be used to check the validity of the window. One possibility would be, for example, to demand at least 50% valid test signal values, but the precise choice typically always depends on the problem at hand and/or the nature of the input signals.

The trend tests that may be used for valid windows include, without being limited to, the Mann trend test, for example. In that case, for each window, the quantity $$C = \sum_{k=1}^{n-1} \sum_{l=k+1}^{n} \operatorname{sign}(y_l - y_k)$$

is calculated, where $$\operatorname{sign}(y_l - y_k) = \begin{cases} 1, & \text{for } y_l - y_k > 0 \\ 0, & \text{for } y_l - y_k = 0 \\ -1, & \text{for } y_l - y_k < 0 \end{cases}$$

describes the signum function.

The hypothesis of a negative trend is confirmed, if $C < -K_{n,p}$, the hypothesis of a positive trend is confirmed, if $C > K_{n,p}$.

where $K_{n,p}$ is the p quantile of Kendall's K statistics. The trend result is calculated individually for each parameter-tuple (L, H).

Figure 2A:
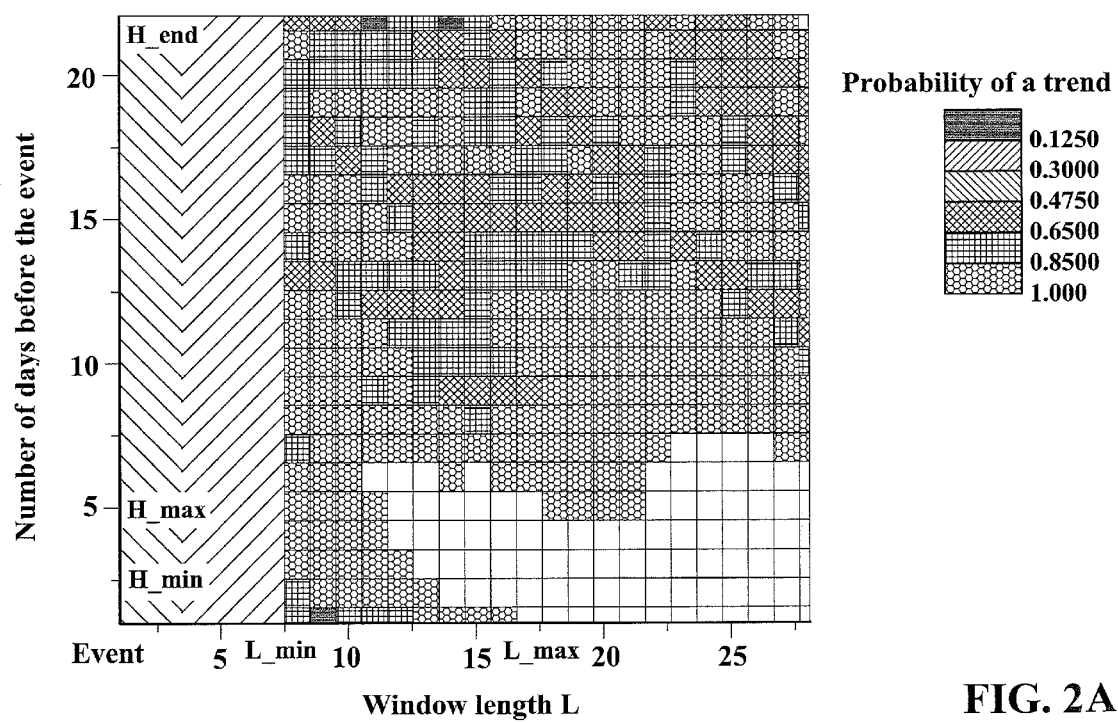
FIG. 2A is a probability of a trend for an event patient as a function of L and H.
Figure 2B:
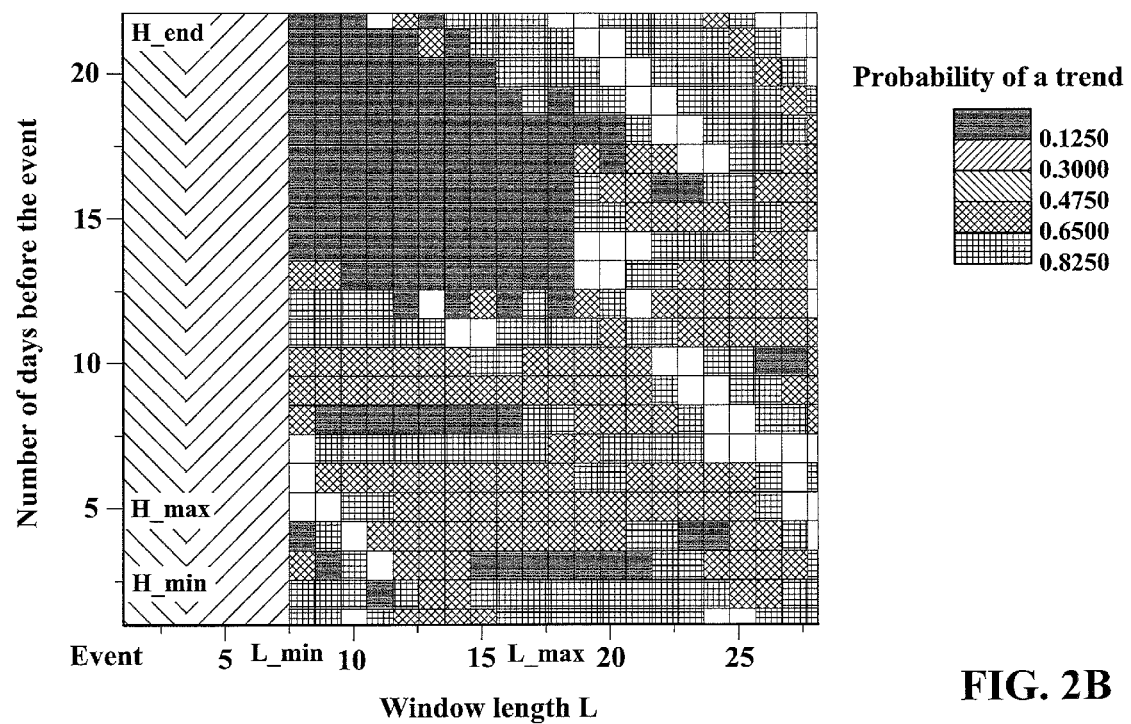
FIG. 2B is a probability of a trend for a control patient as a function of L and H.

For the further course of action, it is advisable to take into account each probability of a trend p for various lengths L of the time windows and for various intervals H between the end of the time window and the event, as shown in FIG. 2 by example for an event patient (FIG. 2A) and a control patient (FIG. 2B) for a primary parameter on the L–H level of the so-called observation plane. Moreover, a positive or negative sign can used to show whether it is an upward or downward trend (+p or –p). $L_{min}$ and $L_{max}$ designated the minimal and maximal lengths of the time windows, $H_{min}$ and $H_{max}$ the minimal and maximal intervals between time of prediction and the event. In the hatched area ($0 \leq L \leq 2$) there is no reason to calculate a trend since a trend always exists for L=2 up to the case of identical measured values. In the area $3 \leq L \leq 7$ a trend calculation does not always lead to a stable result for the problem under consideration. The structure of that observation plane is different for event patients and control patients.

Because of that heterogeneous structure, especially high discriminatory power can be expected in certain areas. The shape, length and size of those areas depend on the relevant primary parameter $S_j$. To determine the shape, length and size of those areas with discriminatory power, the Fischer Score method may be used, among other methods.

If for a given p (H,L) on the observation plane there are data $p_{k,H,L}$, (k=1, ..., m) of two classes (+ and – or event class and control class) with the numbers $n_+$ and $n_-$ of positive and negative class elements, then the Fisher Score is calculated by $$F_{H,L} = \frac{(\overline{p}_{H,L}^+ - \overline{p}_{H,L})^2 + (\overline{p}_{H,L}^- - \overline{p}_{H,L})^2}{\frac{1}{n_+ - 1}\sum_{k=1}^{n_+}(p_{k,H,L}^+ - \overline{p}_{H,L}^+)^2 + \frac{1}{n_- - 1}\sum_{k=1}^{n_-}(p_{k,H,L}^- - \overline{p}_{H,L}^-)^2}$$

with the average of the whole ($\overline{p}_{H,L}$), positive ($\overline{p}_{H,L}^+$) and negative dataset ($\overline{p}_{H,L}^-$) and the $k^{th}$ value of the positive ($p_{k,H,L}^+$) or the negative class ($p_{k,H,L}^-$).

It is also possible to include the probabilities of a trend of several primary parameters as a combined quantity in the calculation of discriminatory powers.

Figure 3:
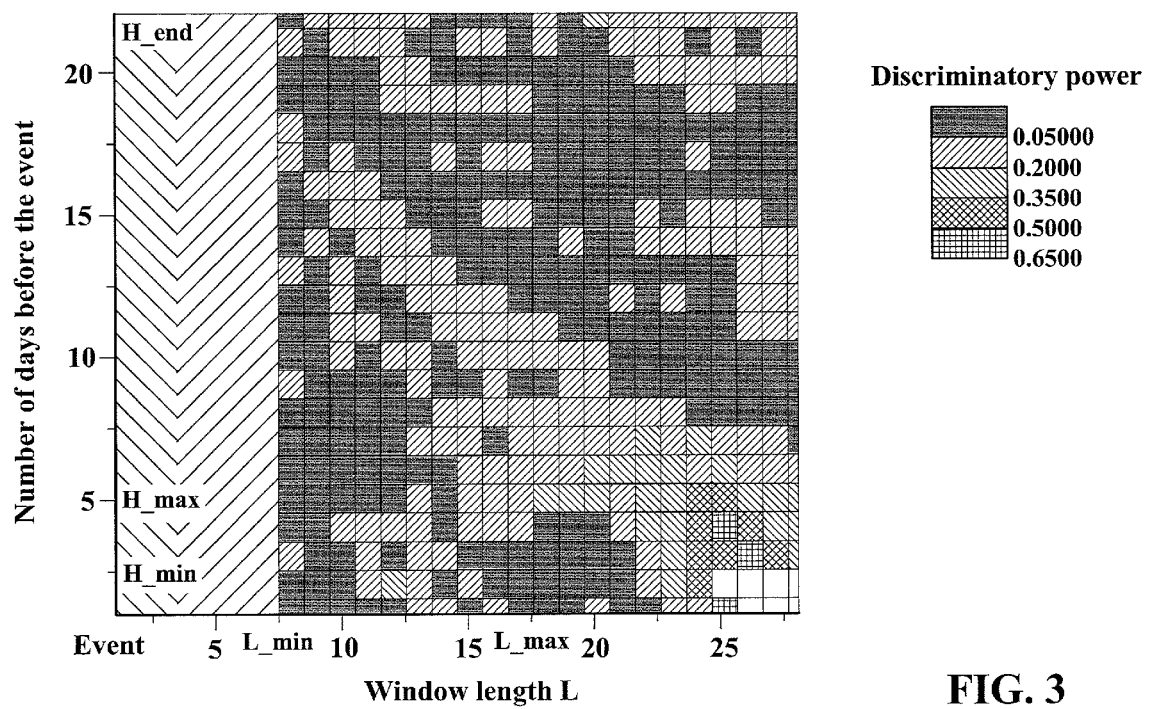
FIG. 3 is a discriminatory power of a primary parameter for a group of patients.
Figure 4:
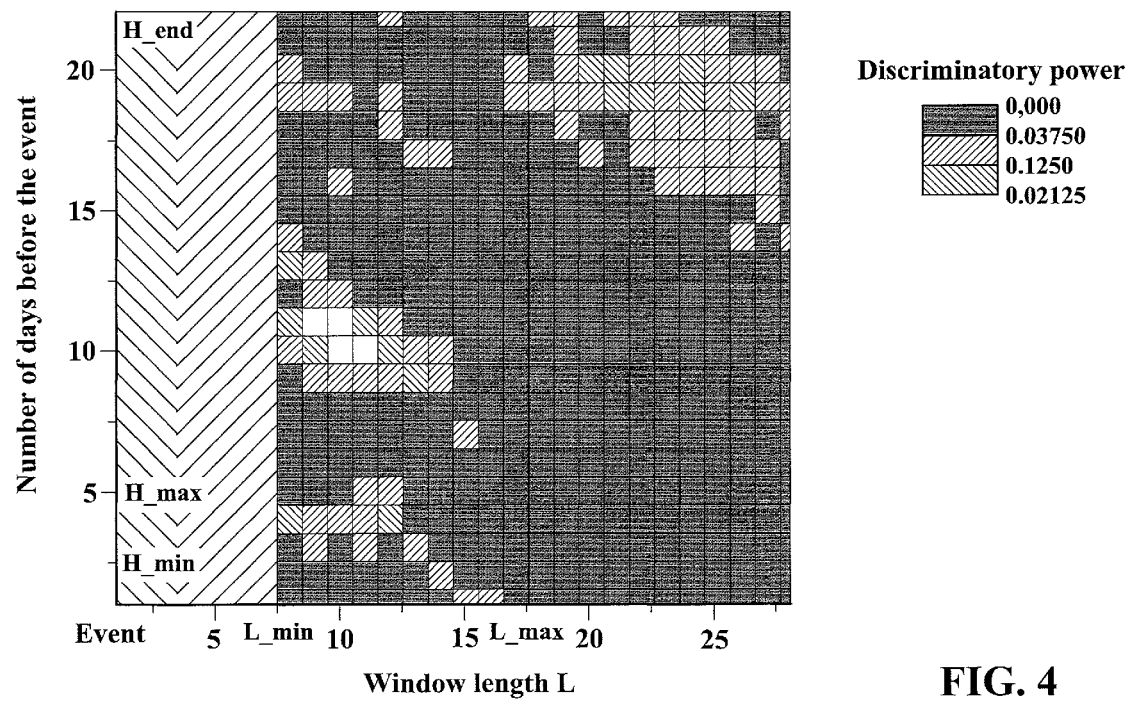
FIG. 4 is an incoherent area of high discriminatory power with a primary parameter.
Figure 5:
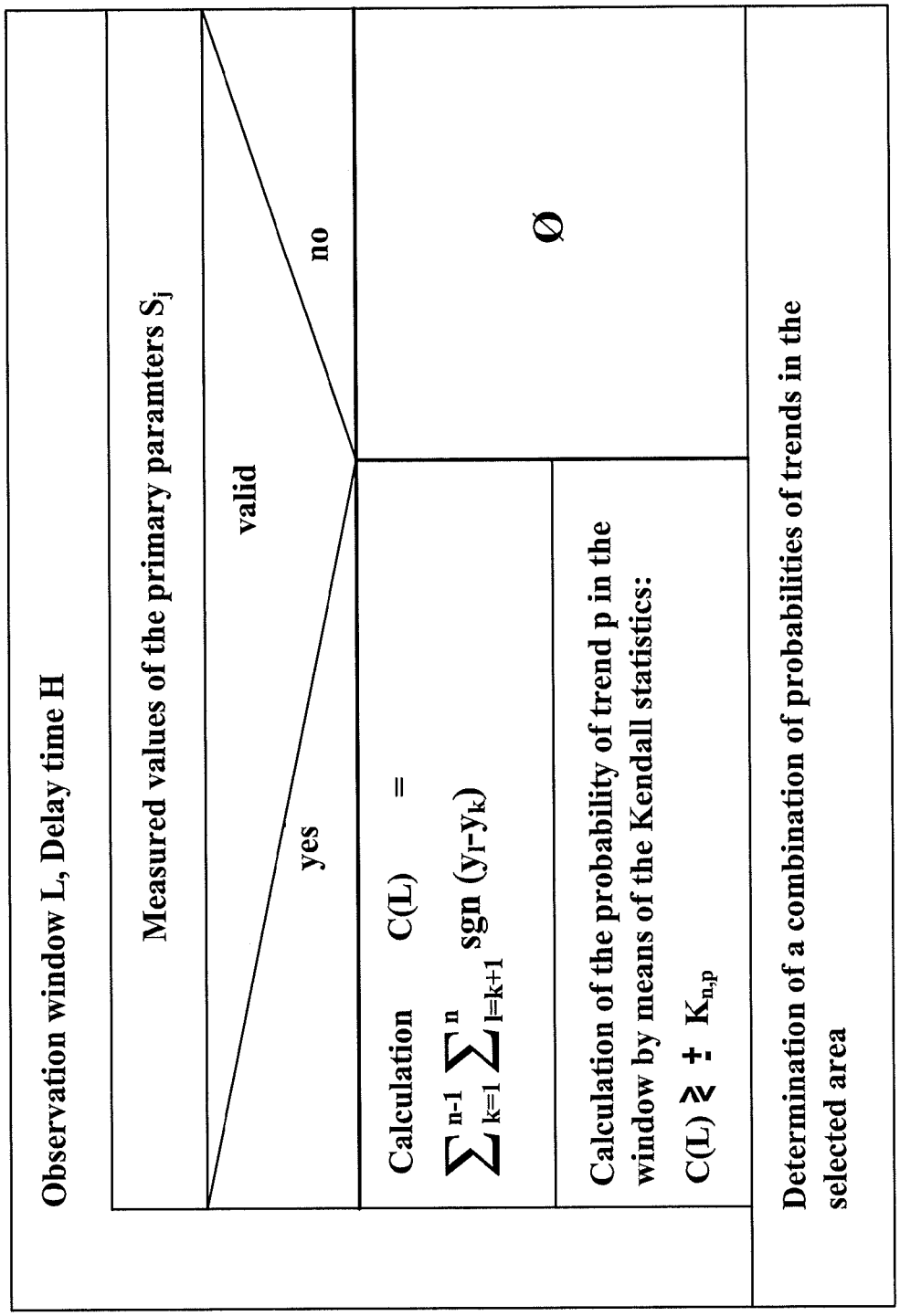
FIG. 5 is a Nassi-Shneiderman diagram for calculating the probabilities of a trend.

For example, FIG. 3 shows the discriminatory power of the primary parameters from FIGS. 2A and 2B for a group of patients. The structure with the areas of high discriminatory power is clearly recognizable here. The quality of the separation between event patients and control patients is higher when special consideration is given to the time windows from the areas of high discriminatory power. They are taken into consideration by weighting the probabilities of a trend from FIG. 2. Those weights may also be represented, among other ways, by a Fischer score function, i.e., by f(F(L,H)). Such weights may vary for different primary parameters. Then the weighted probabilities are combined, e.g., through summation. The area of high discriminatory power for a primary parameter $S_j$ is not necessarily coherent, as can be seen from FIG. 4. FIG. 5 shows a Nassi-Shneiderman diagram for the general calculation of combinations of the probabilities of a trend.

The values thus obtained are so-called Features M with $$M = \sum_{L,H} p(L,H) f(F(L,H))$$

and are therefore suitable for use as input values for classification methods Δ(M). It is sometimes an advantage to input k incoherent areas as features M in the classification. It is likewise sometimes advantageous to include upward and downward trends as special features in the classification. The same is also true of features formed from a combination of several primary parameters.

Optimization Method:

In order to be able to assign the feature quantities to the occurrence of events, it is necessary to use a classification method Δ that itself must be adapted, in turn. For such optimization, for each primary parameter used classified event data and, for example, control datasets without an event are required. To achieve optimal quality of the separation method, it is necessary to use datasets with reliable events and under certain circumstances to select the control data carefully.

For each primary parameter $S_j$ or for at least one primary parameter combination at least one feature M is determined. Features classified in that way are suitable for automated learning as a function of the number of event datasets and control datasets. In that respect, methods such as artificial neuronal networks, support vector machines, hidden Markov models and the like have proved effective. Due to the high number of sets of free parameters during the training process, a large number of classified features are needed during the training process.

If such features are not available in the quantities necessary for such methods, then a classification method must be used in which the number of free parameters is compatible with the number of available training datasets. We shall now proceed to present such a possibility by way of example:

First, the features obtained are used to derive a feature vector $$\vec{M} = (M_1, M_2, \ldots, M_q)$$

which then undergoes scalar multiplication with a classification vector $$\vec{\alpha} = (\alpha_1, \alpha_2, \ldots, \alpha_q).$$

The result of that scalar multiplication is a value for the occurrence of an event. During the training process, for event data or control data the initial value is set to a fixed value $c_{Event}^{Train}$ or $c_{Control}^{Train}$ that lies above or below the training threshold value $c_{0,Train}$. In the subsequent test method, it is necessary to find a $c_{0,Class}$ such that the method achieves a predetermined degree of specificity and/or sensitivity. For the components of the classification vector $\vec{\alpha}$ discrete values (e.g., −1, 0, +1 or a finer grid) may be set in advance in order to further limit the number of degrees of freedom. A maximal interval between $c_{event}$ and $c_{control}$ can be achieved through systematic variation of the components of $\vec{\alpha}$. That classification function in this example is in the form $$\Delta_{Bsp} = \sum_{j=1}^{q} \alpha_j M_j.$$

In general, there is no limitation in this example on a scalar threshold value, so that a hyperplane should be used in $R^n$ as the decision boundary.

Application of the Method:

After completion of the optimization, the classification method can be used to predict an event for the time period to $H_{min}$ to $H_{max}$ that lies in the future relative to the time of prediction. The above-defined features M can be used as input for a selected classification method Δ. A system can now be monitored over time, the method is applied anew each time a new measured value occurs or at larger intervals, in order to make a prediction about the system's deviations from the norm. If the result is greater or less than the threshold value determined in the course of the optimization method $c_{0,Class}$, then, depending on the threshold value, predetermined measures will be launched, such as a therapeutic chain of actions.

Dealing with Invalid and/or Missing Measured Values:

Before the features are generated, the measured values of the measurands used to calculate the features are checked for validity. Certain individual measured values may either be discarded, e.g., because they are shown to be invalid by the validity check, e.g., because they fall outside a predetermined range of values, or they may be missing, because they are lost in some way on the transmission path. The method can deal with invalid and missing measured values in the following manner, for example:

In the case of the Mann trend test according to equation (1), such measured values are ignored by reducing the effective window length by the number of such measured values in such a case.

Void and/or invalid measured values are replaced by corresponding values from an interpolation process.

Probabilities p that cannot be calculated because of void and/or invalid measured values are replaced by a mean value (mean value of the range, mean value of the observation plane, mean value of the group, etc.).

Another possibility of dealing with missing values is used.

We shall now proceed to explain the invention in greater detail using an example of an embodiment.

One example of an embodiment is an apparatus to predict so-called decompensation in patients who suffer from chronic/congestive heart failure (CHF). However, the invention is not limited to the field of medicine. Rather, it can also be used to predict events in other complex systems, such as meteorological or geophysical systems or even in economic systems. Such actions may permit an early action on a problem and resolve an issue at a much lower cost or may permit the early action to be much more effective or much more likely to be effective relative to taking similar actions after the predicted event actually occurs.

It is characteristic of such patients that, despite the generally chronic course of their illness, occasionally phases of an acute and immediately life-threatening condition occur that require hospitalization. Such acute worsening of their chronic heart disease is termed "decompensation". Since hospitalization entails high costs and decompensation is associated with a high degree of mortality and morbidity, an attempt is made to prevent them through early therapeutic intervention. One prerequisite for such early intervention is early identification of the potential decompensation.

A number of CHF patients manifest indications for implantation of an electronic pacing device. That is usually a CRT (Cardiac Resynchronization Therapy) pacemaker to fight directly against the causes of weak cardiac pumping by restoring the ventricular synchronization. To help prevent sudden cardiac death in case of myocardial insufficiency, an automatic defibrillator can also be implanted. With corresponding technical systems, it is possible to determine various measured values of a physiological or technical nature by using the probes and sensors of such implants. Such measured values can either be processed directly in the implant or analyzed by an external computer, for example, while the measured values are sent from the implant telemetrically to the patient's doctor. Other implants and external devices could also be used in this way.

Since a significant percentage of CHF patients are currently receiving electronic implants (CRT-Pacemaker, ICD=Implantable Cardioverter Defibrillator), home monitoring to achieve early recognition of impending decompensation would be desirable. The methodology explained here could also be used for applications unrelated to implants.

Depending on the design, the sensors could contain electrodes to record intracranial electrograms, to determine impedances, pressure and other measured values. The measured values, in turn, could undergo optional intermediate processing or else lead directly to an analysis regarding the diagnosis of a patient. The process of achieving sound diagnostic statements is fraught with a number of difficulties, however.

The basic disease CHF describes a complex patho-physiological process with numerous underlying causes. Ischemic, non-ischemic, cardiomyopathic, toxic and idiopathic causes of CHF are distinguished, for example. Factors such as the patient's failure to take medications as directed or non-adherence to a diet, acute respiratory diseases, infections or other co-morbidities further complicate the description of CHF.

Due to the complexity of CHF and the course of decompensation, the measured patient signals are heterogeneous prior to the occurrence of the events to be observed. That means that different signal behavior can be expected from different patients, and the course of two different decompensation events may turn out differently for one and the same patient. In both cases, gaps in the series of measurement may appear. The cause of such gaps may be that certain measured values were discarded following a validity check or that certain measured values were lost on the telemetry transmission path.

Heterogeneity in signal behavior prior to events extends to several different aspects:

First of all, differences occur regarding which measured values reflect the changes. Thus, it may be the case that the first signs of decompensation appear in the mean heart rate while impedance changes do not appear until the actual decompensation has occurred, but in other cases just the opposite occurs.

Secondly, the patient's reaction to an incipient decompensation depends on behavior to a certain extent. That means that certain measured values may increase in a certain group of patients but decrease in another group; for example, one group becomes more active due to nervousness, whereas another group becomes more withdrawn when anxious.

Third, the time course of disease progression prior to decompensation will generally differ, depending on individual constitution, behavior or other factors. In particular, further unknown, immeasurable, uncontrollable and specific factors may appear in the basic population of CHF patients.

It is necessary to ensure continual monitoring, i.e., to take measurements at least once a day, if possible. Moreover, patients should be spared the stress and costs that may arise when false alarms are given too often and, as a result, the patient is contacted too often and/or hospitalized or even superfluous diagnostic and/or inadequate therapeutic interventions are performed. The methods must therefore have a high degree of specificity, as well, i.e., a very low false alarm rate and thus provide a reliable decision support basis for the physician. In addition, the decompensation of the broadest possible group of patients must be recognized in a timely manner with high sensitivity.

To ensure sufficient statistical quality, it is therefore necessary to use a process that robustly copes with the above-mentioned heterogeneities. In that respect, it also necessary to consider that, because of the nature of the disease, a specific pattern of development of decompensation cannot be known in advance for a given patient.

We shall now proceed to use a selection of parameter values by way of example to show how the method works in one exemplary embodiment.
Observation windows: $L_{min}=8$, $L_{max}=28$
Delay time of the prediction: $H_{min}=1$, $H_{max}=3$, $H_{end}=20$
Number of primary parameters: 8
Weighting function:

$$f(F(L, H)) = \begin{cases} 1 & \text{for } F(l, H) \geq F_0 \\ 0 & sonst \end{cases}$$

Number of features: q=10 (because of two primary parameters with two disjunctive areas)
Required discriminatory powers: $F_{0,1}=F_{0,2}=\ldots=F_{0,10}=0.5$ Specifying the individual boundaries of the areas is highly dependent on the apparatus and would not further facilitate and understanding here.

The primary parameters may be selected, for example, from the following quantity:
- All measured values that include the patient's heart rate, such as the heart rate over a predetermined time period, the heart rate during a specified phase of rest, the variability of the heart rate, and so on.
- All measured values that determine impedances in the patient, whether through intracranial (bipolar and multipolar) or intrathoracic measurements or by determination using external sensors.
- All measured values that determine the patient's activity in any way.
- All measured values that receive as input the percentage of left- or right-ventricular events, whether stimulated, perceived or otherwise.
- All measured values that record implant-dependent signals.
- All measured values that determine extrasystoles, irrespective of their place of origin.
- All measured values that register a patient's hemodynamics or other compliance, pressures, volumes or intervals.
- All measured values that are determined outside an implanted electronic device, such as measured quantities that are acquired from radio-linked sensors, or measured quantities from devices that record data external to the body and communicate such data telemetrically to the evaluation unit.
- All biomedical measured values such as stimulation thresholds, electrode configurations, sensor amplifications or offset values.
- All measured values such as blood sugar levels, other biomarkers or similar quantities.
- All measured values that determine biometric information about the patient.
- All measured values that record additional information about medication.
- All measured values that are determined by electrophysiological or biochemical processes.
- All measured values that record signals from imaging, acoustic or mechanical processes.
- All of the aforementioned measured values that are normalized and/or scaled in advance.
- Possible combinations of several of the aforementioned measured values.

For the above-mentioned parameter values, this results in the following classification function, for example:

$$\Delta_{Bsp} = \sum_{j=1}^{10} \alpha_j M_j.$$

The values of $\alpha_j$ were optimized in the above-described training process following specification of discrete values. A more precise specification of the primary parameters is therefore unnecessary to understand this example of an embodiment.

The embodiments of the invention are not limited to the example of an advantageous embodiment given above. Rather, a number of varieties are conceivable that could also make use of the arrangement according to the invention, the method according to the invention, the computer program according to the invention and the machine-readable storage medium according to the invention in fundamentally different embodiments.

It will be apparent to those skilled in the art that numerous modifications and variations of the described examples and embodiments are possible in light of the above teaching. The disclosed examples and embodiments are presented for purposes of illustration only. Therefore, it is the intent to cover all such modifications and alternate embodiments as may come within the true scope of this invention and the appended claims.

We claim:

1. A non-transitory machine-readable medium storing program instructions executable by a processor to perform a method to predict at least one system event, the method comprising:
   capturing of measured values $s_j$ of at least one primary parameter $S_j$ within at least one time window of preset-table length,
   for at least one part of the captured primary parameters $S_j$, determining a probability of a trend $p_j$ for a number of said time windows that can be set in advance,
   for at least one part of the captured primary parameters $S_j$, determining a value for the relevance of the time windows window for a the prediction of at least one system event,
   for at least one part of the captured primary parameters $S_j$ and for at least one part of the time windows, constructing at least one feature M to describe the system through analysis of the probability of a trend $p'_j$ and of the value for the relevance of the time windows,
   classifying at least one feature M, and
   signaling of a system event and/or initiation of system-event-related measures according to the results of the classifying,
   wherein the probabilities of a trend $p_j$ for time windows of a length L, $L_{min} \leq L \leq L_{max}$, and for times of prediction H, $H_{min} \leq H \leq H_{max}$ are determined.

2. The machine-readable medium according to claim 1, wherein determining the value for the relevance of the time windows includes determining a discriminatory power of the time windows.

3. The machine-readable medium according to claim 1, wherein the analysis of the probabilities of a trend $p_j$ includes a weighting of the probabilities of a trend $p'_j$.

4. The machine-readable medium according to claim 1, wherein a classification method used for the classifying is optimized using classified event data and/or control data.

5. The machine-readable medium according to claim 1, wherein for a given primary parameter $S_j$, several features are constructed using different L-H combinations.

6. The machine-readable medium according to claim 1, wherein in the constructing of at least one feature M, probabilities of upward and downward trends are considered together or separately.

7. The machine-readable medium according to claim 1, wherein in the constructing of at least one feature M, a probability of the trend strength is taken into account.

8. The machine-readable medium according to claim 1, wherein the measured values $s_j$ are supplied by an active or passive implant.

9. The machine-readable medium according to claim 1, wherein the machine-readable medium is implemented into a system comprising a medical system, a meteorological system, a geophysical system, or an economic system.

10. The machine-readable medium according to claim 1, further comprising an active or passive implant to record the measured values $s_j$.

11. A data processing installation having a computer program stored in a non-transitory storage medium of the data processing installation, wherein the computer program is configured to execute a method to predict at least one system event, the method comprising:
- capturing of measured values $s_j$ of at least one primary parameter $S_j$ within at least one time window of presettable length,
- for at least one part of the captured primary parameters $S_j$, determining the probability of a trend $p_j$ for a number of time windows that can be set in advance,
- for at least one part of the captured primary parameters $S_j$, determining a value for the relevance of the time window for the prediction of at least one system event,
- for at least one part of the captured primary parameters $S_j$ and for at least one part of the time windows, constructing at least one feature M to describe the system through analysis of the probability of a trend $p'_j$ and of the value for the relevance of the time windows,
- classifying at least one feature M, and
- signaling of a system event and/or initiation of system-event-related measures according to the results of the classifying,
- wherein the probabilities of a trend $p_j$ for time windows of a length L, $L_{min} \leq L \leq L_{max}$, and for times of prediction H, $H_{min} \leq H \leq H_{max}$ are determined.

12. A method to predict at least one system event, the method comprising:
- downloading from an electronic data network to a non-transitory data processing installation connected to the data network a computer program configured to have the data processing installation perform the steps of:
  - capturing of measured values $s_j$ of at least one primary parameter $S_j$ within at least one time window of pre-settable length,
  - for at least one part of the captured primary parameters $S_j$, determining the probability of a trend $p_j$ for a number of time windows that can be set in advance,
  - for at least one part of the captured primary parameters $S_j$, determining a value for the relevance of the time window for the prediction of at least one system event,
  - for at least one part of the captured primary parameters $S_j$ and for at least one part of the time windows, constructing at least one feature M to describe the system through analysis of the probability of a trend $p'_j$ and of the value for the relevance of the time windows,
  - classifying at least one feature M, and
  - signaling of a system event and/or initiation of system-event-related measures according to the results of the classifying,
  - wherein the probabilities of a trend $p_j$ for time windows of a length L, $L_{min} \leq L \leq L_{max}$, and for times of prediction H, $H_{min} \leq H \leq H_{max}$ are determined.

13. A computer-implemented method for determining a system event comprising:
- measuring at least one variable with at least one sensor, each variable being a variable of a physiological system or a technical system;
- capturing, by at least one data processing installation connected to the at least one sensor, of measured values $s_j$ of at least one primary parameter $S_j$ within at least one time window based on the measured variable;
- for at least one part of the captured primary parameters $S_j$, determining, by the at least one data processing installation, the probability of a trend $p_j$ for a number of time windows that can be set in advance,
- for at least one part of the captured primary parameters $S_j$, determining, by the at least one data processing installation, a value for the relevance of the time window for the prediction of at least one system event,
- for at least one part of the captured primary parameters $S_j$ and for at least one part of the time windows, constructing, by the at least one data processing installation, at least one feature M to describe the system through analysis of the probability of a trend and of the value for the relevance of the time windows,
- classifying, by the at least one data processing installation, at least one feature M, and
- signaling, by the at least one data processing installation, of a system event and/or initiation of system-event-related measures according to the results of the classifying,
- wherein the probabilities of a trend $p_j$ for time windows of a length L, $L_{min} \leq L \leq L_{max}$, and for times of prediction H, $H_{min} \leq H \leq H_{max}$ are determined.

14. The computer-implemented method according to claim 13, wherein the signaling is an output for an alarm indicating malfunctioning of the system or deviations from normal behavior.

15. The computer-implemented method according to claim 13, wherein the at least one data processing installation is remote from the at least one sensor and is wirelessly connected to the at least one sensor.

16. The computer-implemented method according to claim 13, wherein the system event is a predicted event of a medical system, a meteorological system, a geophysical system, or an economic system.

17. The computer-implemented method according to claim 13, wherein the at least one sensor comprises a plurality of sensors configured to obtain intracardial electrogram data for determining impedances and pressure.

* * * * *